(12) United States Patent
Ding

(10) Patent No.: US 7,758,909 B2
(45) Date of Patent: *Jul. 20, 2010

(54) MEDICAL DEVICE WITH POROUS SURFACE FOR CONTROLLED DRUG RELEASE AND METHOD OF MAKING THE SAME

(75) Inventor: Ni Ding, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/851,675

(22) Filed: Sep. 7, 2007

(65) Prior Publication Data

US 2007/0299509 A1    Dec. 27, 2007

Related U.S. Application Data

(63) Continuation of application No. 10/679,057, filed on Oct. 3, 2003, now abandoned, which is a continuation of application No. 09/110,697, filed on Jul. 7, 1998, now Pat. No. 6,652,581.

(51) Int. Cl.
*B05D 1/00* (2006.01)

(52) U.S. Cl. ............ 427/2.24; 427/2.25; 427/458; 427/472; 427/473

(58) Field of Classification Search ......... 427/457, 427/458, 472, 473; 205/109, 118, 122, 131, 205/135, 162, 164, 183, 316, 317, 320, 322
See application file for complete search history.

(56) References Cited

U.S. PATENT DOCUMENTS

| | | | |
|---|---|---|---|
| 3,758,396 A | 9/1973 | Vieth et al | |
| 4,101,984 A | 7/1978 | MacGregor | |
| 4,334,327 A | 6/1982 | Lyman et al. | |
| 4,655,771 A | 4/1987 | Wallsten | |
| 4,657,544 A | 4/1987 | Pinchuk | |
| 4,733,665 A | 3/1988 | Palmaz | |
| 4,800,882 A | 1/1989 | Gianturco | |
| 4,886,062 A | 12/1989 | Wiktor | |
| 4,954,126 A | 9/1990 | Wallsten | |
| 5,061,275 A | 10/1991 | Wallsten et al. | |
| 5,073,365 A * | 12/1991 | Katz et al. | 427/2.24 |
| 5,120,322 A | 6/1992 | Davis et al. | |
| 5,147,370 A | 9/1992 | McNamara et al. | |
| 5,205,921 A | 4/1993 | Shirkanzadeh | |

(Continued)

FOREIGN PATENT DOCUMENTS

WO    WO 95/03083    2/1995

(Continued)

*Primary Examiner*—Erma Cameron
(74) *Attorney, Agent, or Firm*—Fish & Richardson P.C.

(57) ABSTRACT

The medical devices of the invention comprise a portion having a porous surface for release of at least one biologically active agent therefrom. The porous surface is made of a material such as a polymer having a plurality of voids. To load the porous surface with a biologically active agent or drug, an electrophoresis method is employed. In this method, a device having a porous surface is placed into a drug solution or suspension, along with an electrode. An electric current is applied to the device and electrode. Under such a current, the drug, which has a positive or negative charge, will be loaded into the pores or voids of the porous surface.

17 Claims, 2 Drawing Sheets

U.S. PATENT DOCUMENTS

| | | | |
|---|---|---|---|
| 5,304,121 A | | 4/1994 | Sahatjian |
| 5,464,650 A | | 11/1995 | Berg et al. |
| 5,500,013 A | * | 3/1996 | Buscemi et al. ............ 623/1.22 |
| 5,693,085 A | | 12/1997 | Buirge et al. |
| 5,758,562 A | | 6/1998 | Thompson |
| 5,843,172 A | | 12/1998 | Yan |
| 5,968,091 A | * | 10/1999 | Pinchuk et al. ............ 623/1.16 |
| 5,972,027 A | | 10/1999 | Johnson |
| 6,364,856 B1 | * | 4/2002 | Ding et al. ............. 604/103.02 |
| 6,391,052 B2 | | 5/2002 | Buirge et al. |
| 6,635,082 B1 | | 10/2003 | Hossainy et al. |

FOREIGN PATENT DOCUMENTS

| | | |
|---|---|---|
| WO | WO 96/32907 | 10/1996 |

\* cited by examiner

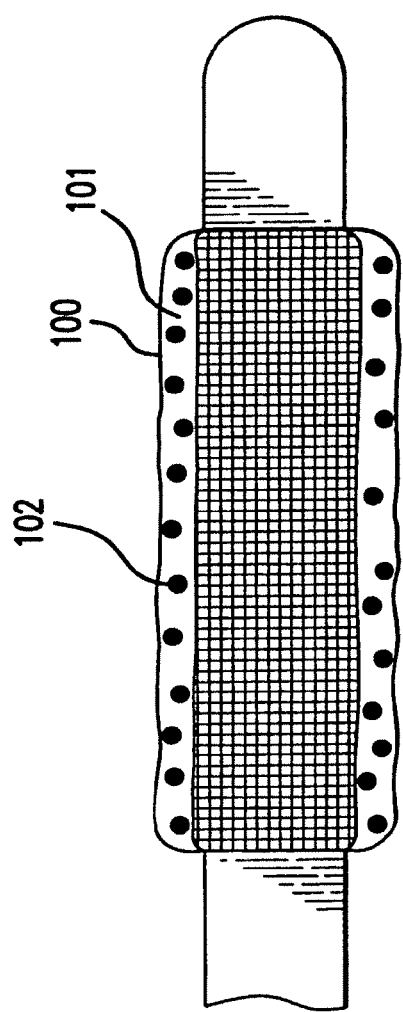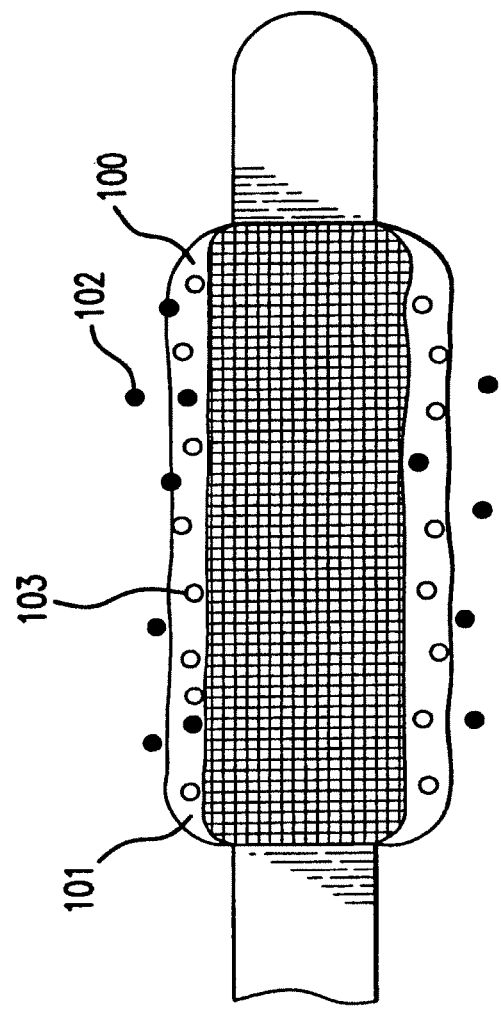

MEDICAL DEVICE WITH POROUS SURFACE FOR CONTROLLED DRUG RELEASE AND METHOD OF MAKING THE SAME

This application is a continuation of application Ser. No. 10/679,057, filed on Oct. 3, 2003, now abandoned which is a continuation of application Ser. No. 09/110,697, filed on Jul. 7, 1998, now U.S. Pat. No. 6,652,581, which applications are incorporated by reference herein in their entirety.

FIELD OF THE INVENTION

This invention relates generally to medical devices for delivering a biologically active agent or drug to a desired location within the body of a patient. More particularly, the invention is directed to medical devices having a porous surface comprising a plurality of voids therein. The porcus surface is capable of being loaded with a drug, e.g., by infusing or placing the drug into the voids, for release into the body, particularly upon expansion of the portion of the medical device with the porous surface. In one method of loading the porous surface, the drug is concentrated into the voids by electrophoresis.

BACKGROUND OF THE INVENTION

For certain diseases which are localized to a particular part of the body, the systemic administration of drugs for the treatment of these diseases is not preferred because of the inefficiencies associated with the indirect delivery of the drugs to the afflicted area. Also, if a drug causes significant side effects, it is generally inappropriate for systemic delivery.

Instead, it is preferred that the drug be directly applied to the diseased tissue. Because such localized delivery to the afflicted area usually requires a relatively small amount of drug, side effects of the drug are reduced. Also, since localized delivery requires smaller amounts of drugs, such delivery is desirable for expensive drugs.

However, such localized delivery of drugs to the walls of lumens, such as blood vessels and ducts, can be problematic since body lumens are generally involved in the transport of body fluids, which tend to carry the drug away from the afflicted area. Thus, there is a need for devices and methods for the localized delivery of drugs to afflicted tissue, especially body lumens.

Also, if a drug or biologically active agent is biologically derived (e.g., a gene, a protein or a lipid), it usually cannot withstand standard sterilization of the device (e.g., ETO, gamma, or e-beam sterilization, autoclaving). Thus, the number of drugs that can be incorporated into the implantable device is limited. Hence, there is a need for a method for including such drugs into a drug-releasing device.

A number of methods for delivering drugs to body lumens or vessels involve the use of catheters having expandable portions, such as a balloon, disposed on the catheter. For instance, U.S. Pat. No. 5,304,121 to Sahatjian, PCT application WO 95/03083 to Sahatjian et al. and U.S. Pat. No. 5,120,322 to Davis et al. describe medical devices in which the exterior surface of the device is coated with a swellable hydrogel polymer. A solution of a drug to be delivered to the afflicted tissue is incorporated into the hydrogel. The drug is usually pre-sterilized by such methods as filtration. The drug is held within the matrix of the hydrogel. In the case where the medical device is a balloon catheter, the drug is delivered by inserting the catheter into the body lumen and expanding the coated balloon against the afflicted tissue of the lumen to force the drug from the hydrogel into the tissue.

However, these hydrogel coated devices have certain disadvantages. In particular, because the loading of the drug into the hydrogel is based on diffusion, the amount of drug that can be loaded onto the devices is limited. Thus, there remains a need for a way to load more drug onto implantable devices.

Other methods for making a drug coated implantable device include ones in which a composition of a drug, a polymeric material and a solvent is applied to at least a surface of the device. Such a method is described in co-pending application Ser. No. 08/633,490, filed Jun. 13, 1996 and published as EP 0 822 788A2 on Feb. 11, 1998. Also, U.S. Pat. No. 5,464,650 to Berg et al. describes drug containing coatings for medical devices.

SUMMARY OF THE INVENTION

These and other objectives are accomplished by the present invention. To achieve the aforementioned objectives, a medical device and a method for making such device for the localized delivery of biologically active agents to a patient has been invented.

The medical devices of the invention comprise a portion which has a porous surface. The porous surface includes the pores and the material between the pores which make up the porous surface. The porous surface is made of a material, such as polymer or a polymer blend, having a plurality of voids therein. The void space of the coating is preferably greater than about 60% of the volume of the porous surface. The porous surface can be a porous coating covering the surface of the device. The thickness of such a coating can be tailored to meet individual needs for release of at least one biologically active agent. Alternatively, the porous surface can be a structural part of the device. For example, a stent graft formed of a porous membrane would have a porous surface. A biologically active agent is loaded into the voids for release when the device is implanted.

In another embodiment of the invention, the medical device is a stent endoprosthesis having at least a portion which is covered with a polymeric porous surface such as a polymeric coating or material with a plurality of voids therein. A biologically active agent or a drug is placed into the voids for controlled release when the stent is implanted or inserted into a body lumen.

In yet another embodiment, the medical device is a stent graft comprising at least one portion which is made of porous graft material, which can, but need not be further covered with a porous or "sponge" coating. A drug is loaded into the voids to form a drug-coated stent graft.

The devices of the present invention can be prepared by applying a porous coating composition to a surface of the device, e.g., stent or stent graft. The porous coating composition comprises a polymer dissolved in a solvent and an elutable particulate material. After the coating is cured, it is exposed to a solvent, e.g., water, which causes the particulate material to elute from the polymer to form a porous or sponge coating having a plurality of voids therein.

The porous surface or coating can be loaded with a drug in an electrophoresis method. In such a method, the drug is dissolved or suspended in a solvent to form a drug solution or suspension. The device and an electrode are placed into the solution or suspension. An electric current source, e.g., battery, is connected to the device and the electrode. When the current source is switched on, the drug (which has a positive or negative charge) in the solution or suspension will be loaded into the voids of the device's porous surface.

Furthermore, prior to placing the device into the drug solution or suspension, the porous surface of the device can already contain materials which do not dissolve in the solution or suspension. Such materials include drugs or radiopaque materials, which permit the device to be visible during implantation under fluoroscopy.

With certain devices which are formed of porous materials, such as a porous stent graft, such devices can be loaded without first applying a porous coating to the graft. However, a porous coating can be used in conjunction with this type of device. A device with such a porous surface can be directly loaded in an electrophoresis method as described above.

DESCRIPTION OF THE DRAWINGS

FIGS. 1a-1b depict a method of preparing a porous coating for a medical device.

DESCRIPTION OF THE PREFERRED EMBODIMENTS

Figure 2:
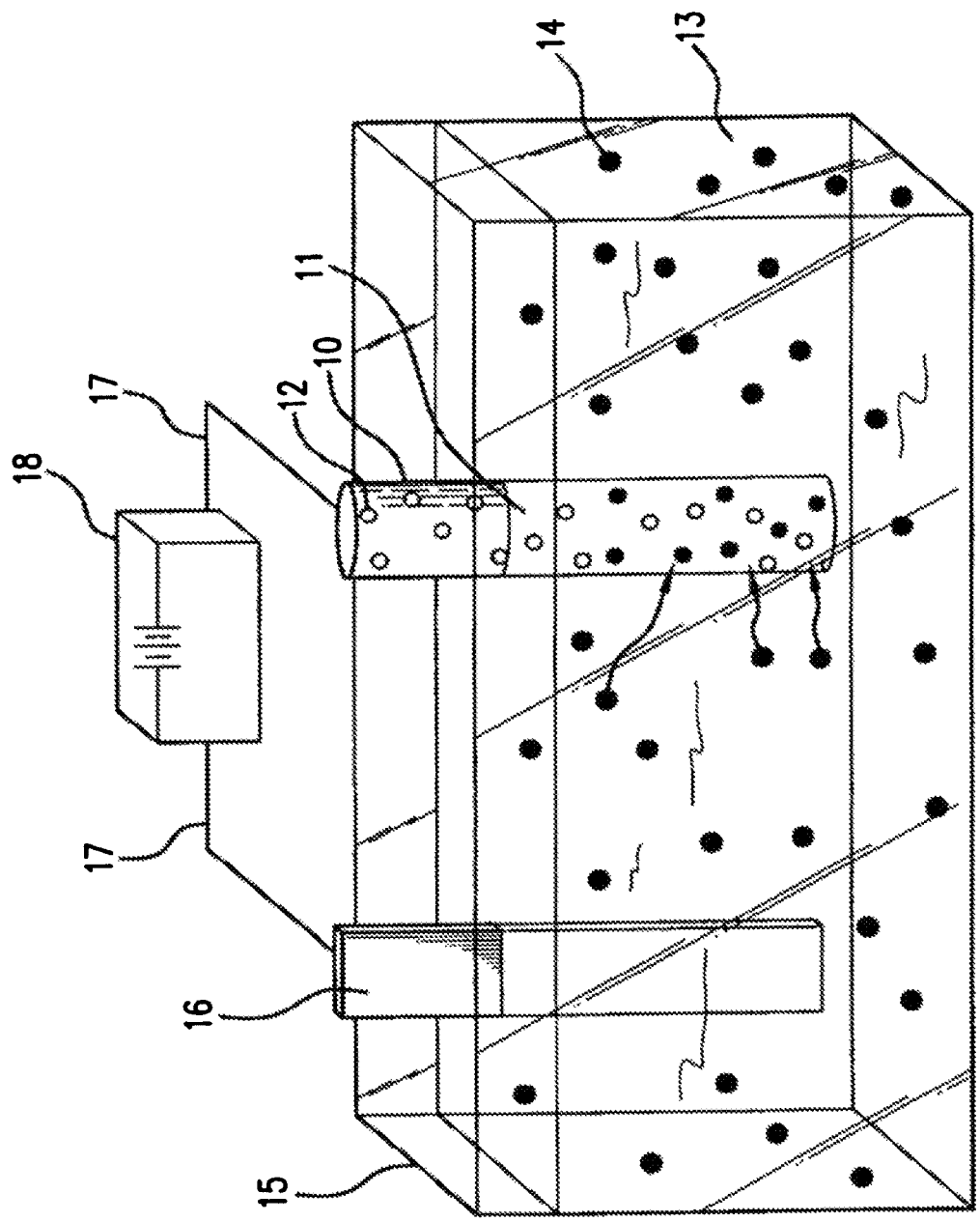
FIG. 2 depicts an electrophoresis method for concentrating a biologically active agent into the porous coating or material.

Devices which can be used in this invention include self-expanding stents and balloon expandable stents. Examples of self-expanding stents useful in the present invention are illustrated in U.S. Pat. Nos. 4,655,771 and 4,954,126 issued to Wallsten and U.S. Pat. No. 5,061,275 issued to Wallsten et al. Examples of appropriate balloon-expandable stents are shown in U.S. Pat. No. 4,733,665 issued to Palmaz, U.S. Pat. No. 4,800,382 issued to Gianturco and U.S. Pat. No. 4,886,062 issued to Wiktor. It will be appreciated that all references cited herein are incorporated by reference in their entireties, for all purposes.

The expandable stent may be formed from polymeric, metallic, ceramic materials and/or composite materials. However, it is preferred that the stent contain a metallic material, e.g., stainless steel, nitinol, tantalum. Suitable polymeric materials include without limitation poly-L-lactic acid, polycarbonate and polyethylene terephthalate.

The stent grafts suitable for the present invention include those appropriate for cardiovascular applications, such as ones described in U.S. Pat. No. 4,657,544 to Pinchuk, or urinary applications, such as U.S. Pat. No. 4,334,327 to Lyman. Generally, such grafts are made of biocompatible polymeric materials, e.g., polyurethane, silicone, polyethylene terephthalate, teflon, or tissue engineered autografts or xenografts. As a result, when these polymeric grafts are used in the claimed electrophoresis method of the invention, it is preferable that the graft include some metallic material to conduct the current and facilitate the concentrating of the drug into the porous surface.

Furthermore, the stent graft can be formed of a porous material having a porous surface, such as a porous membrane. Examples of such stent grafts and methods for making them are described in U.S. Pat. No. 4,657,544 to Pinchuk and U.S. Pat. No. 5,758,562 to Thompson. When such porous stent grafts are used in the electrophoresis method, they can, but do not have to be coated with a porous coating before the grafts are loaded with biologically active agents.

Moreover, other implantable medical devices such as blood oxygenator, heart valves and vein valves can be used in the invention. In general, any implantable device that contains some metal portion can be used.

The following is a more detailed description of suitable materials and methods useful in producing the drug loaded coatings or materials of the invention.

The polymer(s) useful for forming the porous coating should be ones that are biostable, biocompatible, particularly during insertion or implantation of the device into the body and avoids irritation to body tissue. Examples of such polymers include without limitation polyurethanes, polyisobutylene and its copolymers, silicones, and polyesters. Other suitable polymers include polyolefins, polyisobutylene, ethylene-alphaolefin copolymers, acrylic polymers and copolymers, vinyl halide polymers and copolymers such as polyvinyl chloride, polyvinyl ethers such as polyvinyl methyl ether, polyvinylidene halides such as polyvinylidene fluoride and polyvinylidene chloride, polyacrylonitrile, polyvinyl ketones, polyvinyl aromatics such as polystyrene, polyvinyl esters such as polyvinyl acetate; copolymers of vinyl monomers, copolymers of vinyl monomers and olefins such as ethylene-methyl methacrylate copolymers, acrylonitrile-styrene copolymers, ABS resins, ethylene-vinyl acetate copolymers, polyamides such as Nylon 66 and polycaprolactone, alkyd resins, polycarbonates, polyoxyethylenes, polyimides, polyethers, epoxy resins, polyurethanes, rayon-triacetate, cellulose, cellulose acetate, cellulose butyrate, cellulose acetate butyrate, cellophane, cellulose nitrate, cellulose propionate, cellulose ethers, carboxymethyl cellulose, collagens, chitins, polylactic acid, polyglycolic acid, and polylactic acid-polyethylene oxide copolymers.

If the polymer is being applied to a part of the medical device which undergoes mechanical challenges, e.g., expansion and contraction, the polymers are preferably selected from elastomeric polymers such as silicones (e.g., polysiloxanes and substituted polysiloxanes), polyurethanes, thermoplastic elastomers, polyisobutylene and its copolymers ethylene vinyl acetate copolymers, polyolefin elastomers, and EPDM rubbers. The polymer is selected to allow the coating to better adhere to the surface of the expandable portion of the medical device when it is subjected to forces or stress.

Furthermore, although the porous or sponge coating can be formed by using a single type of polymer, various combinations of polymers can be employed. The appropriate mixture of polymers can be coordinated with biologically active agents of interest to produce desired effects when coated on a medical device in accordance with the invention.

The elutable particulate materials which can be incorporated into the polymer include without limitation polyethylene oxide, polyethylene glycol, polyethylene oxide/polypropylene oxide copolymers, polyhydroxyethyl methacrylate, polyvinylpyrrolidone, polyacrylamide and its copolymers, salts, e.g., sodium chloride, sugars, and elutable biologically active agents such as heparin.

The amount of elutable particulate material that is incorporated into the polymer should range from about 10% to 90% by weight of the porous or sponge coating and preferably, from about 30% to 70%. The average particle size of the elutable material can range from 1-100 microns and preferably from about 2 to 15 microns.

The solvent that is used to form the mixture or slurry of polymer and elutable particulate materials include ones which can dissolve the polymer into solution and do not alter or adversely impact the therapeutic properties of the material employed. Examples of useful solvents for silicone include tetrahydrofuran (THF), chloroform and dichloromethane.

The composition of polymer and elutable particulate material can be applied to a portion of the medical device in a variety of ways. For example, the composition can be spray-coated onto the device or the device can be dipped into the composition. One of skill in the art would be aware of methods for applying the coating to the device. The thickness of the porous coating can range from about 10 μm to 0.5 mm. Preferably, the thickness is about 20 μm to 100 μm.

After the composition is applied to the device, it should be cured to produce a polymer containing the particulate material and to evaporate the solvent. Certain polymers, such as silicone, can be cured at relatively low temperatures, (e.g., room temperature) in what is known as a room temperature vulcanization (RTV) process. More typically, the curing/evaporation process involves higher temperatures so that the coated device is heated in a oven. Typically, the heating occurs at approximately 90° C. or higher for approximately 1 to 16 hours when silicone is used. For certain coatings the heating may occur at temperatures as high as 150° C. The time and temperature of heating will of course vary with the particular polymer, drugs, and solvents used. One of skill in the art is aware of the necessary adjustments to these parameters.

To elute the particulate material from the polymer, a solvent is used. The device can be soaked in the solvent to elute the particulate materials. Other methods of eluting the particulate is apparent to those skilled in the art.

The choice of the solvent depends upon the solubility of the elutable particulate material in that solvent. For instance, for water-soluble particulate materials such as heparin, water can be used. For elutable particulate materials which can be dissolved in organic solvents, such organic solvents can be used. Examples of suitable solvents, without limitation, include ethanol, dimethyl sulfoxide, etc.

As shown in FIGS. 1a-1b, in one method for forming the porous coating 100, a mixture or slurry comprising a polymer 101, an elutable particulate material 102 and a solvent is applied to a portion of the medical device. The device is then exposed to an aqueous or organic solvent to elute the particulate material 102 from the polymer 101 to form a plurality of voids 103 in the polymer 101 (FIG. 1b).

Other methods of making a porous coating/membrane are known in the art, such as several phase inversion methods. Examples of these phase inversion methods are: 1) solvent freeze drying; 2) polymer, solvent and non-solvent pore former systems; and 3) thermal processes using a latent solvent. A more detailed description of these methods can be found in R. E. Kesting "Synthetic Polymeric Membranes—A Structural Perspective", JOHN WILEY & SONS, 2D EDITION, which is incorporated herein by reference.

After the porous coating is formed on the device, the medical device can be optionally sterilized. Depending upon the nature of the drug used, sterilization of the device can occur before or after the drug is loaded into the sponge coating. Methods of sterilization are known in the art. For example, the devices can be sterilized by exposure to gamma radiation at 2.5-3.5 Mrad or by exposure to ethylene oxide.

The porous materials or membranes which can be used to form porous stent graft can be made of a polymer. Suitable polymers include polyurethane, silicone, polytetra fluorethylene, polyethylene terephthalate, polyisobutylene and its copolymers, polylactic acid, polyglycolic acid and its copolymers, cellulose and its derivatives. Graft materials can also be biologically derived. For example, collagen, elastin, tissue engineered autografts or xenografts are suitable.

As noted early, it is desirable that the stent graft contain some metallic material to facilitate loading of the coating with a drug by electrophoresis. Such metallic material can be incorporated by laminating or cladding a metal or an metallic alloy onto the porous graft material.

To load the biologically active agent in the porous surface, an electrophoresis method can be used. Specifically, as described in FIG. 2, a graft or other medical device 10 having a porous surface 11 containing voids 12 is placed into a container 15 which holds a solution or a suspension 13 of a drug 14. The drug 14 does not have to be dissolved in a solvent. It can remain as a suspension such as a slurry.

Also placed in the container 15 is an electrode 16, typically made of metal. The electrode 16 and the device 10 with the porous surface 11 are connected, typically by wires 17 to a current source 18, such as a battery. When the current source 18 is switched on, at least some of the drug 14, which contains either a positive or negative charge, is loaded into the voids 12, thereby increasing the amount of the drug at the porous surface. In other words, when an electric field is applied to the solution containing the drug, the charged drug molecules are forced to move toward the electrode with the opposite charge. Depending upon the charge on the drug 14, the device 10 functions as either an anode or cathode. If the drug 14 is negatively charged, e.g., a protein or heparin, the device 10 will function as an anode. If the drug 14 is positively charged, the device 10 will function as a cathode.

Also, the type of electrode 16, i.e., its material, used will depend upon whether the device 10 functions as an anode or cathode. For example, if the device 10 is an anode, an electrode 16 which can function as a cathode is used. Persons skilled in the art are aware of how to select suitable electrodes 16.

Furthermore, by adjusting the pH of the drug solution or suspension 13, the mobility of the drug 14 under the electric current can be varied. Specifically, at different pH levels, the predominant ionic form of the drug 14 will be different. For example, with respect to amino acids, if the pH of the solution or suspension 13 is low, e.g., acidic, the carboxyl group is un-ionized and the amino group is ionized. When amino acids are placed into a solution or suspension 13 with a high pH level, the carboxyl group is ionized and the amino group is un-ionized. Such changes in the ionic form or charge form of the drug 14 affects its mobility under the electric current.

It should be noted that the porous surface of the device can contain some biologically active agent even before the surface is loaded with the drug 14 according to this method. More specifically, prior to placing the devices into the drug solution or suspension 13 the porous surface may already contain materials, such as particulate materials, that provide desirable properties to the device. These materials should not be soluble or elutable in the solvent forming the drug solution or suspension 13. They can include another biologically active agent or radiopaque materials to allow the device to be visible during implantation under fluoroscopy.

As used herein, "biologically active agent" or "drug" refers not only to the molecular or charged form of the biologically active agent or drug but also to formulations containing the same, such as, without limitation, liposomes, emulsions with surfactant and cyclodextrin encapsulations.

Preferably, biologically active agents having an electric charge are used in this invention. However, a neutral or a weakly charged biologically active agent can also be used if it can be converted to a charged moiety. There are a variety of ways for carrying out such a conversion. For instance, one typical method includes forming an emulsion of the drug or drug particle with a surfactant. Examples of surfactants which can be used are, without limitation, fatty acids, phospholipids and sodium cetyl sulfate. In another method, the biologically active agent can be converted to a charged moiety by cyclodextrin encapsulation.

Suitable biologically active agents that can be used in this invention include without limitation glucocorticoids (e.g., dexamethasone, betamethasone), heparin, hirudin, angiopeptin, aspirin, growth factors, oligonucleotides, and, more generally, antiplatelet agents, anti-coagulant agents, antimitotic agents, antioxidants, antimetabolite agents, anti-cancer agents and anti-inflammatory agents could be used. Antiplatelet agents can include drugs such as aspirin. Aspirin is classified as an analgesic, antipyretic, anti-inflammatory and antiplatelet drug. Anticoagulant agents can include drugs such as glycosaminoglycan, protamine, hirudin and tick anticoagulant protein. Glycosaninoglycans include heparin, heparin sulfate, hyaluronic acid, chondroitin, chondroitin sulfate, dermatan sulfate and keratosulfate and their respective derivatives. Antimitotic agents and antimetabolite agents can include drugs such as methotrexate. Antibiotic agents can include penicillin, cefoxitin, and oxacillin. Also, genes or nucleic acids, or portions thereof can be used. Such genes or nucleic acids can first be packaged in liposomes or nanoparticles. Furthermore, collagen synthesis inhibitors, such as tranilast, can be used.

The description contained herein is for purposes of illustration and not for purposes of limitation. Changes and modifications may be made to the embodiments of the description and still be within the scope of the invention. Furthermore, obvious changes, modifications or variations will occur to those skilled in the art. Also, all references cited above are incorporated herein, in their entirety, for all purposes related to this disclosure.

I claim:

1. A method of making a stent comprising:
    forming a porous coating comprising a polymer on a stent substrate; and
    loading a biologically active agent into pores of the porous coating by:
        placing the stent into a solution or suspension including the biologically active agent;
        placing an electrode in the solution or suspension; and
        applying an electric current to the stent and the electrode to facilitate concentrating the biologically active agent into the pores of the porous coating.

2. The method of claim 1, wherein the electrode functions as a cathode and the biologically active agent has a negative charge.

3. The method of claim 1, wherein the electrode functions as an anode and the biologically active agent has a positive charge.

4. The method of claim 1, wherein the stent comprises a metallic material.

5. The method of claim 1, wherein the stent comprises a polymeric material.

6. The method of claim 1, wherein the stent comprises a ceramic material.

7. The method of claim 1, wherein at least some of the pores contain a non-elutable particulate material prior to placing the stent into the solution or suspension.

8. The method of claim 1, wherein the volume occupied by the pores is greater than about 60% of the volume of the porous coating.

9. The method of claim 1, wherein the thickness of the porous coating is 10 μm to 0.5 mm.

10. The method of claim 1, wherein the thickness of the porous coating is 20 μm to 100 μm.

11. The method of claim 1, wherein forming the porous coating comprises depositing a coating composition including the polymer on the stent substrate.

12. The method of claim 11, wherein the coating composition further comprises an elutable particulate material.

13. The method of claim 12, wherein the amount of the elutable particulate material is 10% to 90% by weight of the coating.

14. The method of claim 12, wherein the amount of the elutable particulate material is 30% to 70% by weight of the coating.

15. The method of claim 12, wherein the average particle size of the elutable particulate material is 1 to 100 microns.

16. The method of claim 12, wherein the average particle size of the elutable particulate material is 2 to 15 microns.

17. The method of claim 12, wherein forming the porous coating further comprises eluting the elutable particulate material to form the pores of the porous coating.

* * * * *

UNITED STATES PATENT AND TRADEMARK OFFICE
CERTIFICATE OF CORRECTION

| | |
|---|---|
| PATENT NO. | : 7,758,909 B2 |
| APPLICATION NO. | : 11/851675 |
| DATED | : July 20, 2010 |
| INVENTOR(S) | : Ni Ding |

It is certified that error appears in the above-identified patent and that said Letters Patent is hereby corrected as shown below:

Column 1, paragraph 1, under the title: insert the missing sub-heading --RELATED APPLICATION DATA--.

Signed and Sealed this

Twenty-first Day of September, 2010

David J. Kappos
*Director of the United States Patent and Trademark Office*